United States Patent [19]

Murakami

[11] 4,108,004
[45] Aug. 22, 1978

[54] SELF-PROPELLED PIPE INSPECTING APPARATUS

[75] Inventor: Osamu Murakami, Tokyo, Japan

[73] Assignee: Kett Electric Laboratory, Tokyo, Japan

[21] Appl. No.: 831,020

[22] Filed: Sep. 6, 1977

[30] Foreign Application Priority Data

Sep. 13, 1976 [JP] Japan ............... 51-123093[U]

[51] Int. Cl.² ............................................. G01N 29/04
[52] U.S. Cl. .................................... 73/432 R; 73/622; 73/638
[58] Field of Search ............... 73/432, 622, 625, 628, 73/633, 635, 637, 638, 641; 324/262

[56] References Cited

U.S. PATENT DOCUMENTS

| | | | |
|---|---|---|---|
| 3,299,349 | 1/1967 | Tompkins | 324/262 |
| 3,540,266 | 11/1970 | Lofgren | 73/637 |
| 3,936,733 | 2/1976 | Clary | 324/262 |

*Primary Examiner*—S. Clement Swisher
*Attorney, Agent, or Firm*—Pollock, Vande Sande & Priddy

[57] ABSTRACT

Disclosed is a self-propelled pipe inspection apparatus suitable for use in inspecting a plurality of parallel and vertical pipes one by one, for the presence of faults such as cracking, corrosion and so on, by non-destructive testing method. The apparatus has fault detecting means which may be of conventional type, pipe cramping means adapted to cramp the pipe and a mobile carrier by which the fault detecting means and the pipe cramping means are carried. The mobile carriage has a power-driven running surface which may be a running surface of an endless belt and adapted to be pressed onto the pipe surface when the pipe is cramped by the cramping means. The cramping means comprise at least a pair of arms each of which having a bent end carrying a roller. Each arm is supported for free rotation around its longitudinal axis, so that the roller may be swung outwardly to clear the pipe, when the latter is brought into the space between the pair or arms. In the cramping state, as the running surface of the mobile carriage is driven, the apparatus as a whole moves up and down along the pipe, keeping a resilient contact with the latter. The fault detecting means are secured to the mobile carriage through a turn table for inspecting all circumferential parts of the pipe.

19 Claims, 7 Drawing Figures

SELF-PROPELLED PIPE INSPECTING APPARATUS

The present invention relates to an apparatus for inspecting pipes and, more particularly, to an apparatus for inspecting pipes capable of running along the pipes to be inspected in the axial direction of the latter.

For instance, in the plants for chemical industries, a number of pipes are arranged to run long distances. These pipes have to be inspected or examined periodically for the presence of defects such as breakage, cracking, corrosion and the like.

In the plants for producing ethylene, for example, pipes connected to a furnace for decomposing naphtha are bound to pass naphtha of a temperature as high as 800° ~ 1000° C. Thus, when there is a defect in the pipe such as cracking, the naphtha of the high temperature may dangerously leak out to cause a serious accident. This is the reason why the frequent periodical protective inspection of the pipes is essential.

Conventionally, there have been proposed and used a variety of examination methods such as magnaflux inspection, ultrasonic-wave inspection method and the like. These inspection methods have been selectively used, depending on the material of the pipe, kind of the defect and other factors.

The piping for the aforementioned naphtha-decomposing furnace consists of a number of pipes each of which having a length of 10 to 15 m, disposed in parallel with one another to extend vertically. Therefore, the inspection of these pipes involves a substantial problem that the inspector has to take a labour of travelling a long distance to repeatedly move the detecting apparatus up and down along the number of pipes, one after another.

To cope with this problem, the present inventors have proposed, in the specifications of Japanese Utility Model Application Nos. 43305/1975 and 43306/1975, a self-propelled pipe inspecting apparatus having a pair of mobile units each of which carrying inspecting instrument. These units are adapted to be propelled by a motor, along the objective pipe cramped therebetween.

This self-propelled inspecting apparatus has been generally acceptable in that it can diminish the labour required for the insepction to a certain extent, but still has a drawback that it takes a considerably long time for attaching the apparatus to the pipe to be inspected. More specifically, each unit has rollers for engaging the pipe surface, which renders the apparatus complicated massive and voluminous. Therefore, the attaching of the apparatus to the pipe is made in such a manner that one person stands at each side of the pipe, holding each one of the mobile units and assembles the units into the complete self-propelled apparatus cramping the pipe to be inspected therebetween. In addition, this apparatus has to be separated into two units at each time of the attaching and detaching to and from the pipe, which is very troublesome.

Further, since the apparatus is propelled by itself through rollers driven by a motor and engaging the pipe surface, the rollers often make slip on the pipe surface to cause a propulsion failure. This slip can be avoided only through increasing the number of rollers, which, in turn, leads to a disadvantages of increased weight and volume of the apparatus. In addition, since the surfaces of the rollers are concaved to meet the curvature of the pipe surface, parts of a roller have different peripheral velocities depending on their radii. This means that most parts of each roller is obliged to make slips resulting in a rapid wear of rollers. Furthermore, a troublesome work is necessary to replace the rollers with new ones having a curvature of concaved surface well meeting the new diameter of the objective pipe.

It is therefore an object of the invention to overcome above described problems inherent in the prior arts by providing an improved self-propelled pipe inspecting apparatus which is compact, light-weighted and capable of being attached to the objective pipe only by one person.

It is another object of the invention to provide a self-propelled pipe inspecting apparatus which can run along the pipe without substantial slip of the rollers.

To these ends, according to the invention, there is provided a self-propelled pipe inspecting apparatus having means for detecting faults, means for cramping the objective pipe and a mobile carriage for carrying these means. The cramping means includes at least two arms extending outwardly of the mobile carriage. The outer ends of these arms are bent at a certain angle to the axis of the arms and carry rollers adapted for engagement with the objective pipe surface. The arms are supported at their ends opposite to the bent ends, movably along and rotatably around the longitudinal axes of respective arms, and are biased by resilient means so that the arms are retracted toward the body of the apparatus. The mobile carriage is provided with an elastic running surface adapted for cooperation with the rollers in cramping the pipe therebetween. The apparatus thus can run along the pipe, cramping the latter by its rollers and elastic running surface.

More specifically, the running surface of the mobile carriage incorporated in the pipe inspecting apparatus of the invention is constituted by an elastic endless belt or a plurality of elastic rollers disposed in parallel with one another.

These and other objects, as well as the advantageous features of the invention will become more clear from the following description of the preferred embodiments taken in conjunction with the attached drawings in which:

Figure 1:
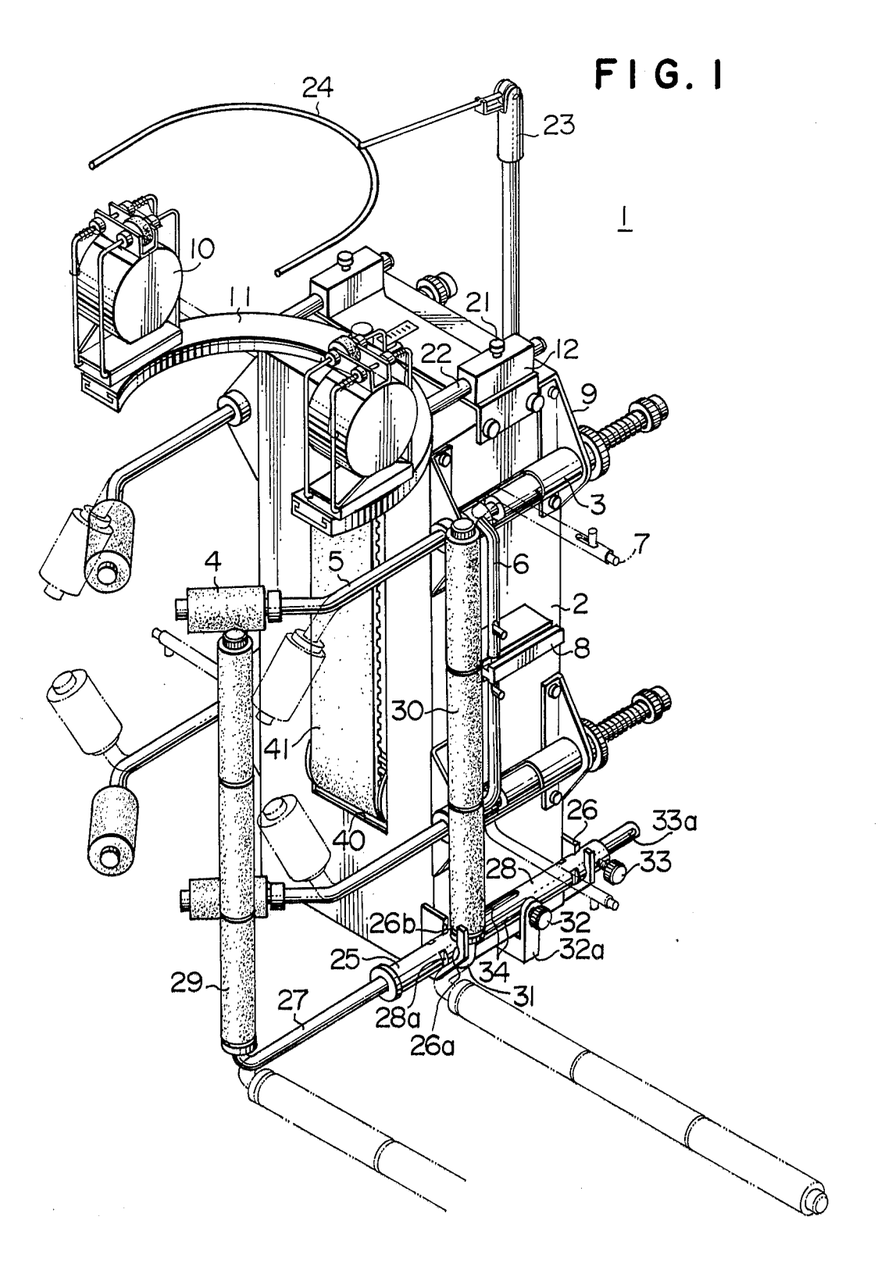
FIG. 1 is a perspective view of a self-propelled pipe inspecting apparatus embodying the present invention.

Referring at first to FIG. 1 showing a perspective view of a self-propelled pipe inspecting apparatus embodying the invention, two cramping means 3 for cramping the pipe to be inspected are secured to each side of a mobile carriage 2, by means of respective brackets 9. The cramping means 3 will be described later in more detail.

Each cramping means 3 is provided with an arm 5 carrying at its bent end a roller 4. The arm 5 is supported for free rotation around its longitudinal axis, with respect to the mobile carriage 2. Thus, the roller 4 can be swung laterally to the outside of the mobile carriage 2. Therefore, the inspecting apparatus can be attached to a pipe to be inspected by at first rotating the arms 5 to turn the horizontally disposed rollers 4 to extend vertically, so that they may clear the pipe, inserting the pipe into the space between the arms 5 and then turning the arms 5 to allow the rollers 4 to resume the horizontal posture, thereby to cramp the pipe between the rollers 4 and the mobile carriage 2.

The rotation of the arm 5 is caused by a pivotal movement of a handle 6. The handle 6 has at its end a lock 7 the end of which is adapted to be received by a groove formed in an arm stopper, so as to lock the rollers 4 at the operating position, i.e. the cramping position.

The mobile carriage 2 has at its upper end two fault detecting means 10 positioned to oppose to each other. These fault detecting means are mounted on a semi-circular table 11 which is secured to the top surface of the mobile carriage through a bracket 12. The bracket 12 has longitudinal bores each of which slidably receives a rod 22. The rods 22 are fixed at their ends remote from the bracket to the table 11.

This arrangement allows the table 11 to move back and forth relatively to the mobile carriage 2. Screws 21 are provided for locking the table 11 at a suitable position. Therefore, two detecting means 10 can be located to oppose diametrically to each other, in accordance with various diameters of the pipes to be inspected. Further, the table 11 may preferably be moved laterally, in the similar manner, with respect to the mobile carriage 2.

Figure 4:
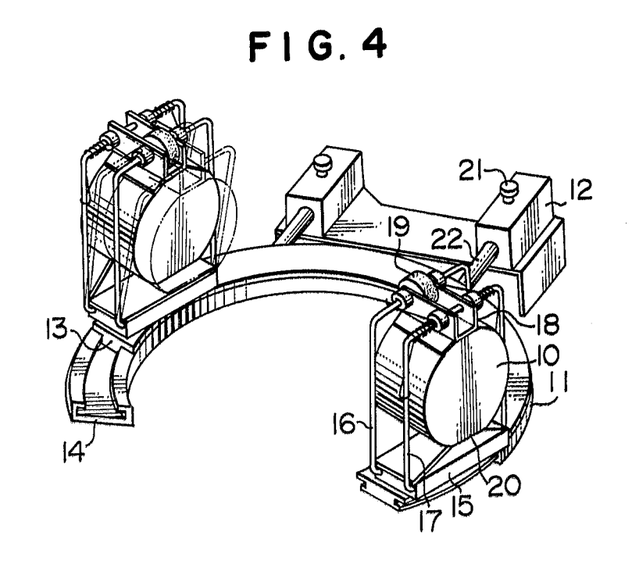
FIG. 4 is an illustration showing the detail of a fault detector and a table on which the detector is mounted.

In addition, as will be seen from FIG. 4, the table 11 is constituted by a slide 13 and a cooperating slide guide 14. More specifically, the slide 13 has both side protrusions which are slidably received by respective side grooves formed at the inside of the slide guide 14. Thanks to this arrangement, the slide 13 can be slided along the slide guide 14 in the circumferential direction, so that the detecting means 10 carried by the slide 13 may be moved in the circumferential direction, over an angle greater than 90°, to any desired position around the pipe.

Each detecting means is suspended from two inversed U-shaped bars 16, 17, through a channel member 18. The bars 16, 17 have hooked ends which are inserted into side bores of a mount 15 fixed to the slide 13 of the table 11. A wheel 19 is rotatably carried by the inversed U-shaped bar 16, and is received by the channel of the channel member 18, at the front portion of the latter. The mount 15, two inversed U-shaped bars 16, 17 and the channel member 18 in combination constitute a parallelogram toggle link mechanism, which can be deformed keeping the horizontal posture of the channel member 18. Consequently, the detecting means 10 suspended from the channel members 18 can be moved to and from the pipe, keeping their front faces in parallel with each other. Thus, the front faces of the detecting means 10 are kept in parallel with the wall of the objective pipe, in spite of the possible fluctuation of the diameter of the pipe. Since the detecting means 10 on each parallelogram toggle link mechanism is so positioned as to locate the centroid at a front portion of the latter, the toggle mechanism is adapted to be swung inwardly, when the toggle mechanism is released, due to the force of gravity. However, when not used, the detecting means 10 is held at a resting position, by means of a leaf spring 20 which engages a hooked recess formed in the lower peripheral surface thereof.

For putting the detecting means into operating position, the leaf spring 20 is depressed to disengage the detecting means from the hooked recess, so that the detecting means 10 is naturally moved inwardly, due to the gravity, until the wheel 19 carried by the channel member 18 comes into contact with the peripheral wall of the pipe. This wheel 19 is kept in contact with the pipe wall, and rolls on the latter when the inspection apparatus runs along the pipe, preserving a constant clearance between the front face of the detecting means 10 and the peripheral wall of the pipe.

Turning again to FIG. 1, a detector 23 is provided on a rear upper portion of the mobile carriage 2, for detecting the upper end of the pipe under inspection. In the illustrated embodiment, this detector is constituted by a link mechanism having a U-shaped bar 24 adapted to surround the pipe in order to detect a fitting secured to the upper end of the pipe. The link mechanism is so associated with a microswitch that the latter is switched off to stop the running of the inspection apparatus when the apparatus has come up to bring the U-shaped bar into contact with the fitting of the pipe. Although only one pipe end detector 23 is provided for detecting the upper end of the pipe in the illustrated embodiment, the mobile carriage 2 can have another detector 23 at its lower portion, for detecting the lower end of the pipe.

Guiding means 25 are secured to one side of the mobile carriage 2, at the lower portion of the latter, through brackets 26. The guiding means 25 have a shaft 27 axially slidably received by a sleeve 28 and having one end bent at right angle. A set of guide rollers 29 are secured to the bent end of the shaft 27. Another set of guide rollers 30 is mounted to extend in parallel with the guide rollers 29, on a shaft 31 which is fixed to the sleeve 28 by means of, for example, wedling.

A pair of elongated grooves 34 are formed in the peripheral wall of the sleeve 28, so as to extend in parallel with the longitudinal axis of the sleeve 28. At the same time, grooves 28a are provided at a front and a rear portions of the sleeve 28, so as to extend at right angle to the longitudinal axis of the sleeve 28.

Each bracket 26 has a bore 26a having an inner diameter substantially equal to the outer diameter of the sleeve. The bore 26a opens in the periphery of the bracket 26, through a notch 26b. The guiding means 25 are attached by at first making the grooves 28a of the sleeve 28 align with the notches 26b, and then sliding fitting the sleeve 28 into the bores 26a of the bracket 26. The sleeve 28 fitted in the bore 26a can be freely moved axially and rotatively, within the bores.

The mobile carriage 2 has a supporting member 32a into which driven is a screw 32 for engagement with either one of the elongated grooves 34 of the sleeve 28. It will be seen that the sleeve 28 is locked against the rotation and the axial movement, when the screw 28 is further driven to be received one of these grooves, so as to fix the guide rollers 29, 30 at a retracted position as illustrated by full line or at an operating position as shown by broken line in FIG. 1.

A screw 33 is provided for locking the guide rollers relatively to each other, with an adjustable distance left therebetween. Namely, the screw 33 is adapted to be driven through a threaded bore formed at the rear end of the sleeve 28 into engagement with the shaft 27 of the guide rollers 29. A more safe locking effect will be ensured when a longitudinal groove 33a is formed at the rear end portion of the shaft 27 for receiving the end of the screw 33.

Figure 2:
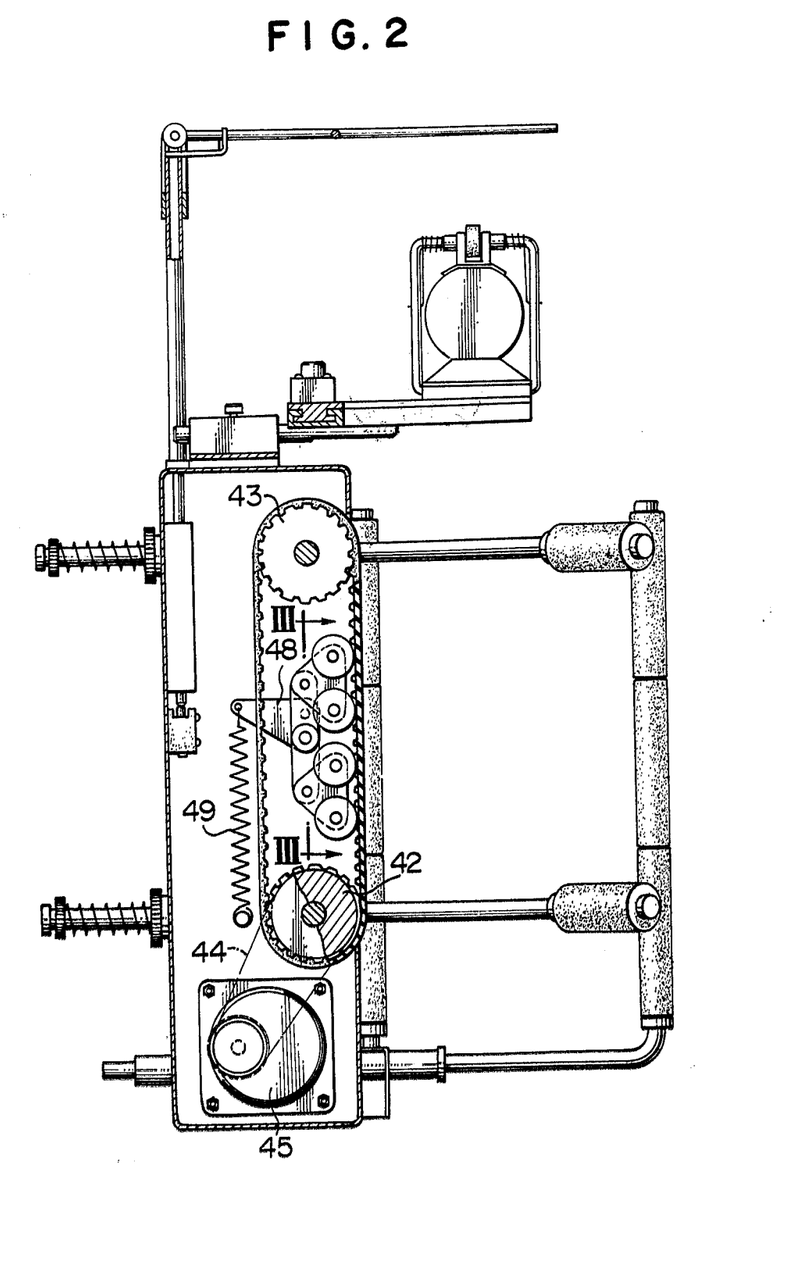
FIG. 2 is a side elevational sectional view of the pipe inspecting apparatus as shown in FIG. 1.

In the illustrated embodiment, the guide means 25 are intended for engagement with a pipe adjacent to and extending in parallel with the pipe under inspection. To this end, the guide rollers 29 and 30 are adapted to be laid, in the operating condition, at right angle to the direction in which the mobile carriage 2 moves, so as to cramp the adjacent pipe therebetween, thereby to preventing the inspection apparatus from oscillating around the pipe during the inspection. The guide means 25 can be optionally detached from the mobile carriage 2, by loosening the screw 32. The guide rollers 29, 30 are preferably swung to the resting position as shown by full line in FIG. 2, during attaching the inspection apparatus to one of a plurality of parallel pipes, so that they may not hinder the attaching.

The sleeve 28 may be provided with a stopper for limiting the swinging of the guide rollers 29, 30, so as to prevent the guide rollers 29, 30 coming into contact with the detecting means 10.

The front wall of the mobile carriage 2 is notched to form a rectangular opening 40, through which emerges the running surface of an elastic endless belt 41.

The arrangement is such that the running surface of the endless belt 41 makes a frictional engagement with the wall of the pipe, when the latter is cramped between the rollers 4 of the cramping means and the mobile carriage, i.e. when the inspection apparatus is correctly attached to the pipe to be inspected. It will be seen that the mobile carriage, i.e. the inspection apparatus as a whole runs along the pipe, when the endless belt 41 is driven by a suitable driving source.

In the illustrated embodiment, the endless belt 41 is constituted by a timing belt having an inner surface having a series of convexities and concavities, going round pulleys or sprockets 42, 43. The sprocket 42 is adapted to be driven by a motor 45, through a chain 44.

Figure 3:
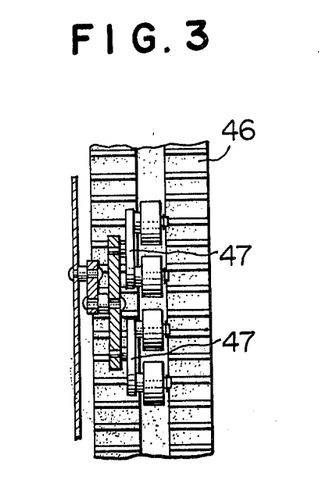
FIG. 3 is a detailed illustration of a relationship between an elastic endless belt and an idle roller assembly which are shown in FIG. 2.

As will be seen from FIG. 3, the convexities and concavities are formed on the inner surface of the endless belt 41 only at both side portions of the latter, so as to form a longitudinal groove 46 at the center of the belt. The groove 46 accommodates an idle roller assembly 47 which is adapted to stretch the belt outwardly, through a lever 48 by a resilient force exerted by a spring 49, thereby to ensure the frictional engagement of the running surface of the endless belt 41 with the pipe surface, when the inspecting apparatus is fitted to the objective pipe.

Figure 5:
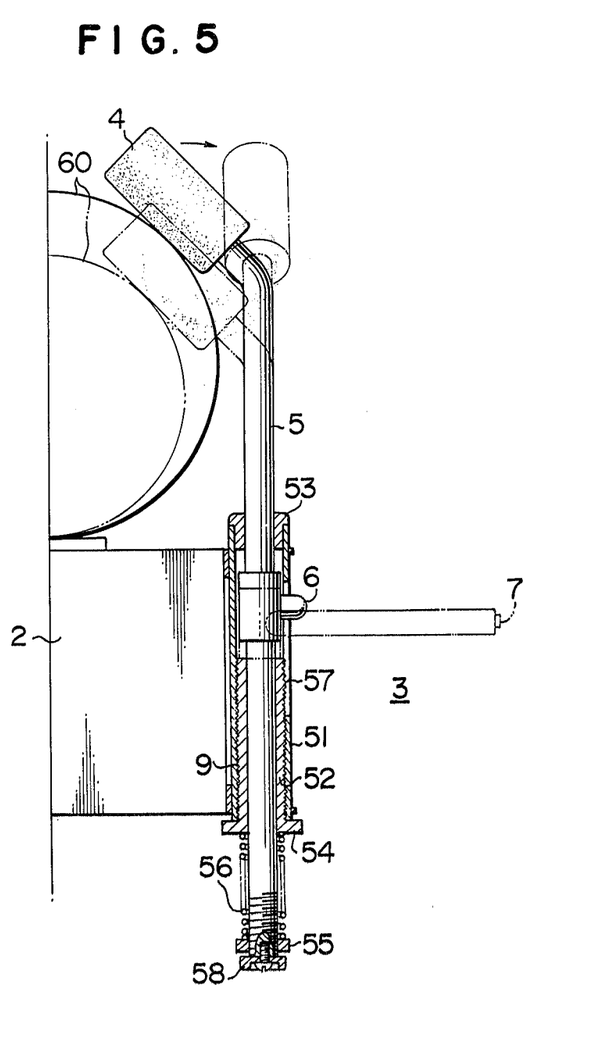
FIG. 5 shows partially in section the detail of a part of cramping means.

Referring now to FIG. 5 showing a partial section of the cramping means 3, the arm 5 carrying the roller 4 at its one end, has the other end passed and extended through a cylindrical body 51. The front end of the cylindrical body 51 is closed by a plug 53 fitted thereto, while the rear end of the cylindrical body 51 is threaded to receive a sleeve 52 having a flanged end 54. A spring 56 is provided to act between the flanged end 54 and the flanged rear end 55 of the arm 5, so as to resiliently bias the arm 5 rearwardly. Consequently, the roller 4 at the end of the arm is biased toward the mobile carriage 2, so that the pipe is resiliently cramped by the rollers 4 and the endless belt 41 of the mobile carriage 2, during the inspection, irrespective of the change or fluctuation of the diameter of the pipe.

However, when the pipe diameter fluctuates or changes too largely, the sleeve 52 is screwed or unscrewed into or out of the cylindrical body 51, so as to displace the arm 5 through the spring 56. The position of the rollers 4 relative to the mobile carriage 2 is thus adjustable, in accordance with the diameter of the pipe to be inspected.

It will be seen that the spring 56 can play the double role of imparting a resilient cramping force for cramping the pipe and absorbing the impact or shock applied to the inspecting apparatus when the latter passes a certain irregularity on the pipe surface or a portion of the pipe at which the diameter abruptly changes, thereby to ensure the safe cramping of the pipe during the inspection running.

The flanged end 55 provided at the rear end of the arm 5 is screwed into the latter. Thus, the distance between the flange 54 of the sleeve 52 and the flange 55 of the arm can suitably be adjusted by screwing and unscrewing the flanged end 55, so as to impart a suitable preload to the spring 56 acting between these flanges. A stopper 58 is attached to the rear end of the arm 5, by means of a screw, for limiting the flanged end 55.

A portion of the wall of the cylindrical body 51 is notched to form an elongated bore 57, through which extended outwardly is a handle 6 fixed to the arm 5. The roller 4 is swung to the position as shown by a dot-and-dash line, as the handle 6 is rotated to the position of the dot-and-dash line, so as to facilitate the attaching of the apparatus to the pipe to be inspected. A slight change of the pipe diameter can conveniently absorbed by the spring 56 which affords an automatic adjustment of the distance between the rollers 4 and the mobile carriage 2. More specifically, assuming that the diameter of the pipe 60 is reduced as illustrated, the roller 4 is displaced to the position as shown by two-dots-and-dash line, by suitably adjusting the sleeve 52.

Figure 6:
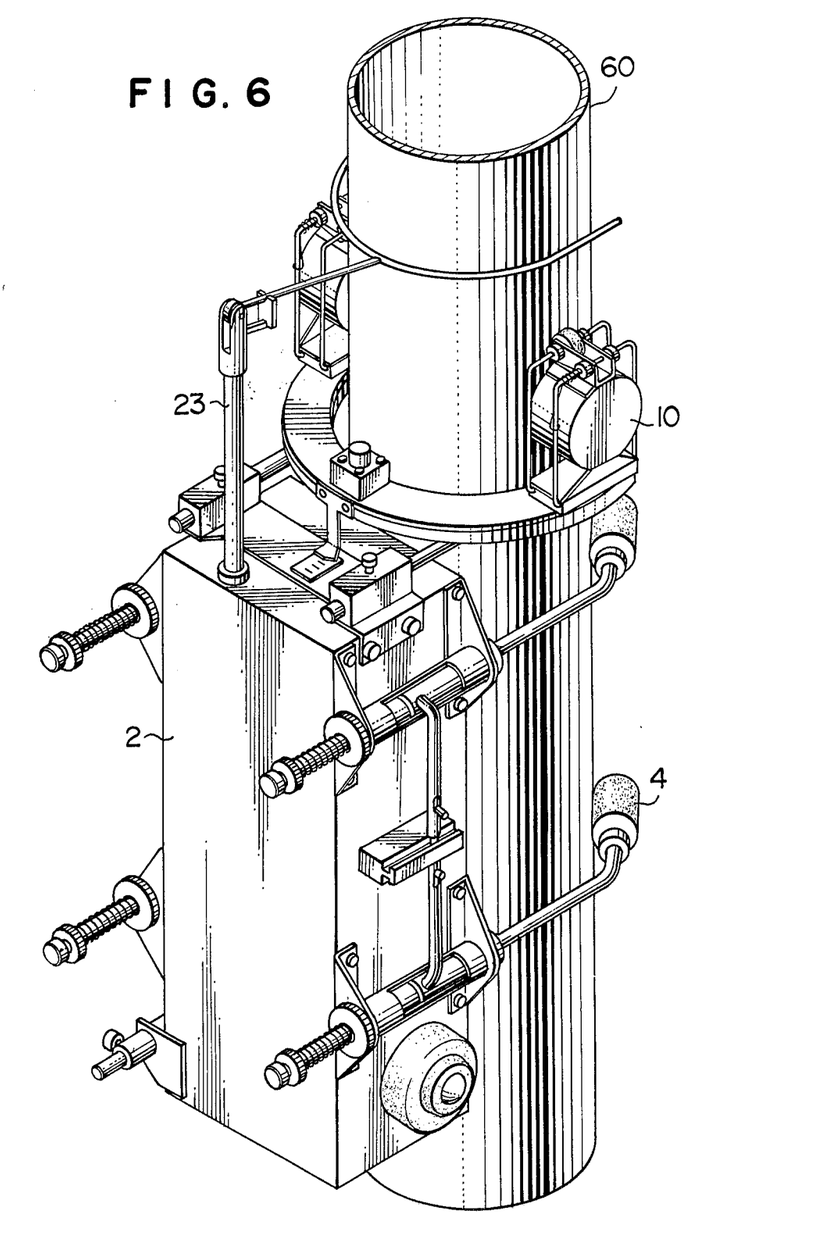
FIG. 6 is an illustration showing the manner in which the self-propelled pipe inspecting apparatus is attached to the pipe to be inspected.

FIG. 6 shows the pipe inspection apparatus attached to the pipe 60 to be inspected.

Figure 7:
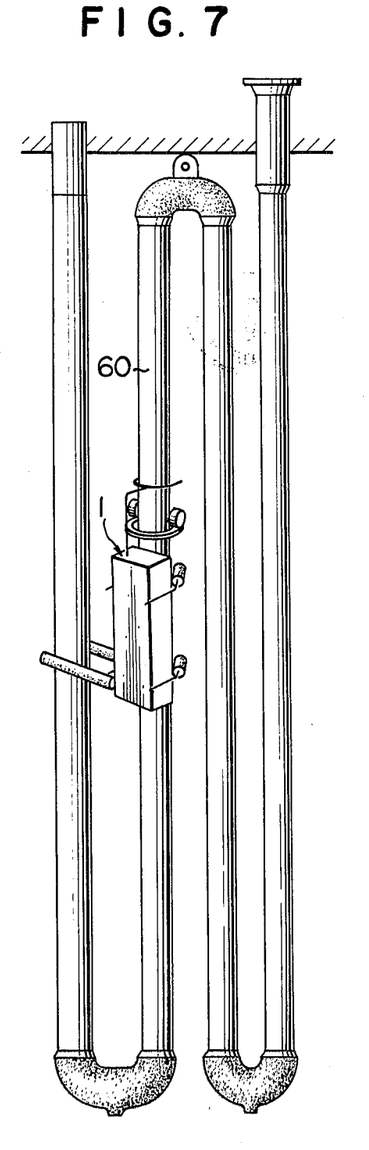
FIG. 7 is a schematic illustration of the manner in which the pipe is inspected for any defect or fault by the self-propelled pipe inspecting apparatus in accordance with the invention.

The pipe inspection apparatus of the invention is intended mainly for inspecting a plurality of parallel pipes extending vertically, as shown in FIG. 7, one by one. The apparatus at first runs upwardly along the pipe until the detector 23 of the apparatus comes to detect the upper end of the pipe. Then the detector 23 acts to reverse the apparatus so that the latter comes to run downwardly. It will be seen that all circumferential portions of the pipe can be inspected without any troublesome, by suitably turning the table 11, so as to change the positions of the detecting means 10. The inspecting apparatus itself is never turned, since the guide rollers 29 and 30 lock the apparatus against the turning by cramping the adjacent pipe.

Although the table 11 is shown to be turn manually in the illustrated embodiment, it is of course possible to turn the table by a suitable power, under a control of a suitable means which may be the detector 23.

Having described the invention through a specific illustrated embodiment, it is to be noted here that the described embodiment is not exclusive, and various changes and modifications may be imparted thereto without departing from the spirit of the invention.

For instance, the elastic running surface of the mobile carriage 2 may be constituted by a plurality of parallel elastic rollers, instead of the described endless belt 41. At the same time, the spring 56 of the cramping means may be substituted by hydraulic resilient means. The detecting means 10 may be designed to be biased toward the pipe wall by resilient means such as springs, rather than by the gravity. Further, the surfaces rollers 4 may be covered with an elastic material.

Other changes and modifications are still possible, within the scope of the invention which is delimited solely by the appended claims.

What is claimed is:

1. A self-propelled pipe inspecting apparatus comprising (a) fault detecting means, (b) pipe cramping means, and (c) a mobile carriage, and characterized in that (a) said cramping means include at least two arms extending outwardly of said mobile carriage; the outer ends of said arms being bent at a certain angle to the axis of respective arms; said bent ends of said arms carrying rollers engageable with a pipe to be inspected; the other ends of said arms being secured to said mobile carriage so that said ends are movable along and rotatable around the longitudinal axes of respective arms; and said arms being biased by resilient means so as to retract said rollers toward said mobile carriage, and in that (b) said mobile carriage has an elastic running surface; a pipe to be inspected being held between said biased rollers of said cramping means and said resilient running surface; whereby said mobile carriage can run along said pipe in the lengthwise direction of the latter.

2. An apparatus as claimed in claim 1, wherein said elastic running surface consists of a running surface of an endless resilient belt stretched between sprockets.

3. An apparatus as claimed in claim 1, wherein said mobile carriage is provided with detachable guiding means for preventing turning of the mobile carriage.

4. An apparatus as claimed in claim 3, wherein said guiding means are guided by a pipe running in parallel with the pipe under inspection.

5. An apparatus as claimed in claim 1, wherein said faults detecting means consist of at least two units disposed on a table rotatable over more than 90° in relation to said mobile carriage.

6. An apparatus as claimed in claim 5, wherein a driving means for rotating said table is provided.

7. An apparatus as claimed in clain 5, wherein said table is a sliding means consisting of upper and lowr semicircular members slidably secured to each other.

8. An apparatus as claimed in claim 5, wherein said table is secured to said mobile carriage for sliding motion in the longitudinal and transverse directions in relation to said mobile carriage.

9. An apparatus as claimed in claim 1, wherein said mobile carriage is provided with a detector adapted to stop the apparatus or switch the running direction of said mobile carrier, upon detecting the pipe end.

10. An apparatus as claimed in claim 6 wherein said driving means for rotating said table is controlled by the motions of said detector.

11. An apparatus as claimed in claim 2, wherein said endless belt has at least one biasing idle roller resiliently provided in said mobile carriage so that the inner surface of said endless belt is outwardly stretched out over whole almost intermediate portion thereof with respect to the length thereof, which idle rollers press said endless belt against said pipe to be inspected.

12. An apparatus as claimed in claim 11, wherein said endless belt is a timing belt having projections in both edge portions of the inner surface thereof with the intermediate portion having no projections of said inner surface of said endless belt contacted with said idle roller.

13. An apparatus as claimed in claim 1, wherein said fault detecting means have at least one gap retaining wheel engageable with a pipe to be inspected, which wheels serve to keep constant the gap between said detector and said pipe to be inspected.

14. An apparatus as claimed in claim 5, wherein said fault detecting means are secured to said table via a parallelogram toggle link mechanism thereby to allow said detecting means to be moved in parallel to said pipe to be inspected.

15. An apparatus as claimed in claim 13, wherein said gap retaining wheel is provided at the front end of a top portion of said parallelogram toggle link mechanism so that said wheel is surely engaged with said pipe to be inspected at the front surface of said detecting means positioned relatively to said pipe to be inspected so that said front surface is a predetermined distance apart from and parallel to said pipe to be inspected.

16. An apparatus as claimed in claim 15, wherein said fault detecting means are mounted on said parallelogram toggle link mechanism so that said detecting means are biased by its force of gravity toward said pipe to be inspected.

17. An apparatus as claimed in claim 15, wherein said detecting means is mounted on said parallelogram toggle link mechanism so that said fault detecting means are biased by a resilient means toward said pipe to be inspected.

18. An apparatus as claimed in claim 16 wherein said parallelogram toggle link mechanism is provided with a leaf spring, which is engaged to said fault detecting means so as to keep the latter at rest when said detecting means is not in operating condition.

19. An apparatus as claimed in claim 1, wherein said elastic running surface is formed by a plurality of elastic rollers.

* * * * *